US00PP21371P2

(12) United States Plant Patent
Hooijman

(10) Patent No.: US PP21,371 P2
(45) Date of Patent: Oct. 5, 2010

(54) *GYPSOPHILA* PLANT NAMED 'ESM GENESIS'

(50) Latin Name: *Gypsophila hybrida*
Varietal Denomination: Esm genesis

(75) Inventor: Aloysius A. J. Hooijman, Aalsmeer (NL)

(73) Assignee: Esmeralda Breeding B.V., Aalsmeer (NL)

( * ) Notice: Subject to any disclaimer, the term of this patent is extended or adjusted under 35 U.S.C. 154(b) by 0 days.

(21) Appl. No.: 12/387,556

(22) Filed: May 4, 2009

(51) Int. Cl.
*A01H 5/00* (2006.01)

(52) U.S. Cl. ..... Plt./354

(58) Field of Classification Search ..... Plt./354
See application file for complete search history.

*Primary Examiner*—Kent L Bell
(74) *Attorney, Agent, or Firm*—C. A. Whealy

(57) ABSTRACT

A new and distinct cultivar of *Gypsophila* plant named 'Esm Genesis', characterized by its erect, straight and moderately strong flowering stems; early, uniform and freely flowering habit; small luminous white-colored flowers with numerous petals; and good postproduction longevity.

1 Drawing Sheet

Botanical designation: *Gypsophila hybrida.*
Cultivar denomination: 'Esm Genesis'.

BACKGROUND OF THE INVENTION

The present invention relates to a new and distinct cultivar of *Gypsophila* plant, botanically known as *Gypsophila hybrida*, grown commercially as a cut flower, and hereinafter referred to by the name 'Esm Genesis'.

The new *Gypsophila* plant is a product of a planned breeding program conducted by the Inventor in El Quinche, Pichincha, Ecuador. The objective of the breeding program is to create new freely and uniformly flowering *Gypsophila* cultivars with many petals per flower and straight stems.

The new *Gypsophila* plant originated from a cross-pollination made by the Inventor in El Quinche, Pichincha, Ecuador in August, 2002 of a proprietary selection of *Gypsophila hybrida* identified as Line 33, not patented, as the female, or seed, parent with a proprietary selection of *Gypsophila hybrida* identified as Line 19, not patented, as the male, or pollen, parent. The new *Gypsophila* was discovered and selected by the Inventor as a flowering plant from within the progeny of the stated cross-pollination in a controlled environment in El Quinche, Pichincha, Ecuador in April, 2003.

Asexual reproduction of the new *Gypsophila* plant by cuttings in a controlled environment in El Quinche, Pichincha, Ecuador since June, 2003, has shown that the unique features of this new *Gypsophila* plant are stable and reproduced true to type in successive generations.

SUMMARY OF THE INVENTION

Plants of the new *Gypsophila* have not been observed under all possible environmental conditions. The phenotype may vary somewhat with variations in environment such as temperature, daylength and light intensity, without, however, any variance in genotype.

The following traits have been repeatedly observed and are determined to be the unique characteristics of 'Esm Genesis'. These characteristics in combination distinguish 'Esm Genesis' as a new and distinct cultivar of *Gypsophila:*

1. Erect, straight and moderately strong flowering stems.
2. Early, uniform and freely flowering habit.

3. Small luminous white-colored flowers with numerous petals.
4. Good postproduction longevity.

In side-by-side comparisons conducted in El Quinche, Pichincha, Ecuador, plants of the new *Gypsophila* differed from plants of the female parent selection in the following characteristics:

1. Plants of the new *Gypsophila* had more erect flowering stems than plants of the female parent selection.
2. Flowers of plants of the new *Gypsophila* were more luminous white than flowers of plants of the female parent selection.

In side-by-side comparisons conducted in El Quinche, Pichincha, Ecuador, plants of the new *Gypsophila* differed from plants of the male parent selection in the following characteristics:

1. Plants of the new *Gypsophila* were taller than plants of the male parent selection.
2. Plants of the new *Gypsophila* were more freely flowering than plants of the male parent selection.
3. Plants of the new *Gypsophila* had more erect peduncles than plants of the male parent selection.
4. Flowers of plants of the new *Gypsophila* had more petals than flowers of plants of the male parent selection.

Plants of the new *Gypsophila* can also be compared to plants of the *Gypsophila* 'Dangypmini', disclosed in U.S. Plant Pat. No. 10,964. In side-by-side comparisons conducted in El Quinche, Pichincha, Ecuador, plants of the new *Gypsophila* differed from plants of 'Dangypmini' in the following characteristics:

1. Plants of the new *Gypsophila* were more narrow than plants of 'Dangypmini'.
2. Flowering stems of plants of the new *Gypsophila* were more erect than flowering stems of plants of 'Dangypmini'.
3. Plants of the new *Gypsophila* had longer internodes than plants of 'Dangypmini'.
4. Plants of the new *Gypsophila* had shorter leaves than plants of 'Dangypmini'.

5. Plants of the new *Gypsophila* had fewer flowers than plants of 'Dangypmini'.

BRIEF DESCRIPTION OF THE PHOTOGRAPH

The accompanying photograph illustrates the overall appearance of the new *Gypsophila* plant. This photograph shows the colors as true as it is reasonably possible to obtain in colored reproductions of this type. Colors in the photograph may differ slightly from the color values cited in the detailed botanical description which accurately describe the colors of the new *Gypsophila* plant. The photograph comprises a side perspective view of a typical flowering stem of 'Esm Genesis' (upper left); close-up view of a typical inflorescence of 'Esm Genesis' (lower left); close-up views of typical flowers of 'Esm Genesis' (upper right and center right); and close-up view of typical leaves of 'Esm Genesis' (lower right).

DETAILED BOTANICAL DESCRIPTION

The aforementioned photographs and following observations and measurements describe plants grown in El Quinche, Pichincha, Ecuador in ground beds in an outdoor nursery and under conditions and practices which approximate those generally used in commercial cut *Gypsophila* production. During the production of the plants, day temperatures ranged from 11° C. to 28° C. and night temperatures ranged from 5° C. to 11° C. Plants were pinched one time about five weeks after planting and were grown under long day/short day conditions. Measurements and numerical values represent averages for typical 17-week old flowering plants. In the following description, color references are made to The Royal Horticultural Society Colour Chart, Fourth Edition, 2001, except where general terms of ordinary dictionary significance are used.

Botanical classification: *Gypsophila hybrida* 'Esm Genesis'.

Commercial classification: Cut flower *Gypsophila*.

Parentage:

*Female, or seed, parent.*—Proprietary selection of *Gypsophila hybrida* identified as Line 33, not patented.

*Male, or pollen, parent.*—Proprietary selection of *Gypsophila hybrida* identified as Line 19, not patented.

Propagation:

*Type.*—By cuttings.

*Time to initiate roots.*—About 16 to 21 days at 17° C. to 25° C.

*Time to produce a rooted young plant.*—About five to six weeks at 17° C. to 25° C.

*Root description.*—Medium in thickness, fibrous; close to 164A in color.

*Rooting habit.*—Freely branching.

Plant description:

*Appearance.*—Perennial cut flower; erect, straight and moderately strong flowering stems; inverted triangle form; early, uniform and freely flowering habit; small luminous white-colored flowers with numerous petals arranged in symmetrical compound cymes; vigorous growth habit.

*Branching habit.*—When pinched, about 23 flowering stems develop per year.

*Plant height.*—About 100 cm.

*Plant diameter or spread.*—About 55 cm.

*Flowering stems.*—Length: About 95 cm. Diameter: About 4 mm. Internode length: About 5.7 cm. Strength: Moderately strong. Texture: Glabrescent. Color: Close to 146A.

Foliage description:

*Arrangement.*—Opposite, decussate, simple; sessile.

*Length.*—About 5.2 cm.

*Width.*—About 1.6 cm.

*Shape.*—Lanceolate.

*Apex.*—Acute.

*Base.*—Cuneate.

*Margin.*—Entire.

*Texture, upper and lower surfaces.*—Smooth, glabrous; waxy.

*Venation pattern.*—Parallel.

*Color.*—Developing leaves, upper and lower surfaces: Close to 139A. Fully expanded leaves, upper surface: Between 139A and 147A; venation, close to 147A. Fully expanded leaves, lower surface: Close to 137A; venation, close to 137B.

Flower description:

*Flower arrangement and habit.*—Symmetrical and uniform compound cymes with numerous small luminous white-colored flowers, flowers rotate; freely flowering habit, about 2,000 flowers per inflorescence; flowers face mostly upright.

*Flowering response.*—In Ecuador, plants flower year round; early flowering habit; plants begin flowering about 15 to 16 weeks after planting.

*Post-production longevity.*—As a cut flower, flowers last for about ten to twelve days; on the plant, flowers last for about 26 to 30 days; flowers persistent.

*Fragrance.*—Slightly fragrant; pleasant.

*Inflorescence height.*—About 95 cm.

*Inflorescence diameter.*—About 38 cm.

*Flower diameter.*—About 6 mm.

*Flower depth (height).*—About 5 mm.

*Flower buds.*—Length: About 2 mm. Diameter: About 2 mm. Shape: Nearly globose. Color: Close to 147A; towards the apex, close to 186A.

*Petals/petaloids.*—Quantity per flower: About 21 to 26 arranged in clusters. Length: About 4 mm. Width: About 2 mm. Shape: Oval to spatulate. Apex: Truncate, emarginate or obtuse. Margin: Entire. Texture, upper and lower surfaces: Smooth, glabrous; waxy. Color: When opening and fully opening, upper surface: Close to NN155D; color becoming closer to 155A with development. When opening and fully opening, lower surface: Close to NN155D.

*Sepals.*—Quantity per flower: About five fused to form a cupped star-shaped calyx. Length: About 2.2 mm. Width: About 1.1 mm. Shape: Roughly lanceolate. Apex: Acute. Margin: Entire. Texture, upper and lower surfaces: Smooth, glabrous. Color: When developing, upper surface: Close to 147A. When developing, lower surface: Close to 147A tinted with close to 186A. Fully developed, upper surface: Close to 146A. Fully developed, lower surface: Close to 147A.

*Peduncles:.*—Length: About 4.7 cm. Diameter: About 4.5 mm. Strength: Strong. Angle: About 44° from vertical. Texture: Smooth, glabrous. Color: Close to 137A.

*Pedicels.*—Length: About 4 mm. Diameter: About 0.4 mm. Strength: Moderately strong. Angle: About 48° from vertical. Texture: Smooth, glabrous. Color: Close to 147A.

*Reproductive organs.*—Stamens: Quantity per flower: About ten. Anther shape: Reniform to globose. Anther length: Less than 1 mm. Anther color: Close to 162A. Pollen amount: Scarce. Pollen color: Close to 162A. Pistils: Quantity per flower: One. Pistil length: About 4.7 mm. Style length: About 3.1 mm. Style color: Close to NN155D. Stigma shape: Curved apiculate. Stigma color: Close to NN155D. Ovary color: Close to 144B; towards the apex, close to N199B. Seed/fruit: Seed and fruit production has not been observed.

Disease/pest resistance: Plants of the new *Gypsophila* have not been shown to be resistant to pathogens and pests common to *Gypsophila*.

Temperature tolerance: Plants of the new *Gypsophila* have been observed to tolerate temperatures ranging from about 7° C. to about 30° C.

It is claimed:

1. A new and distinct *Gypsophila* plant named 'Esm Genesis' as lustrated and described.

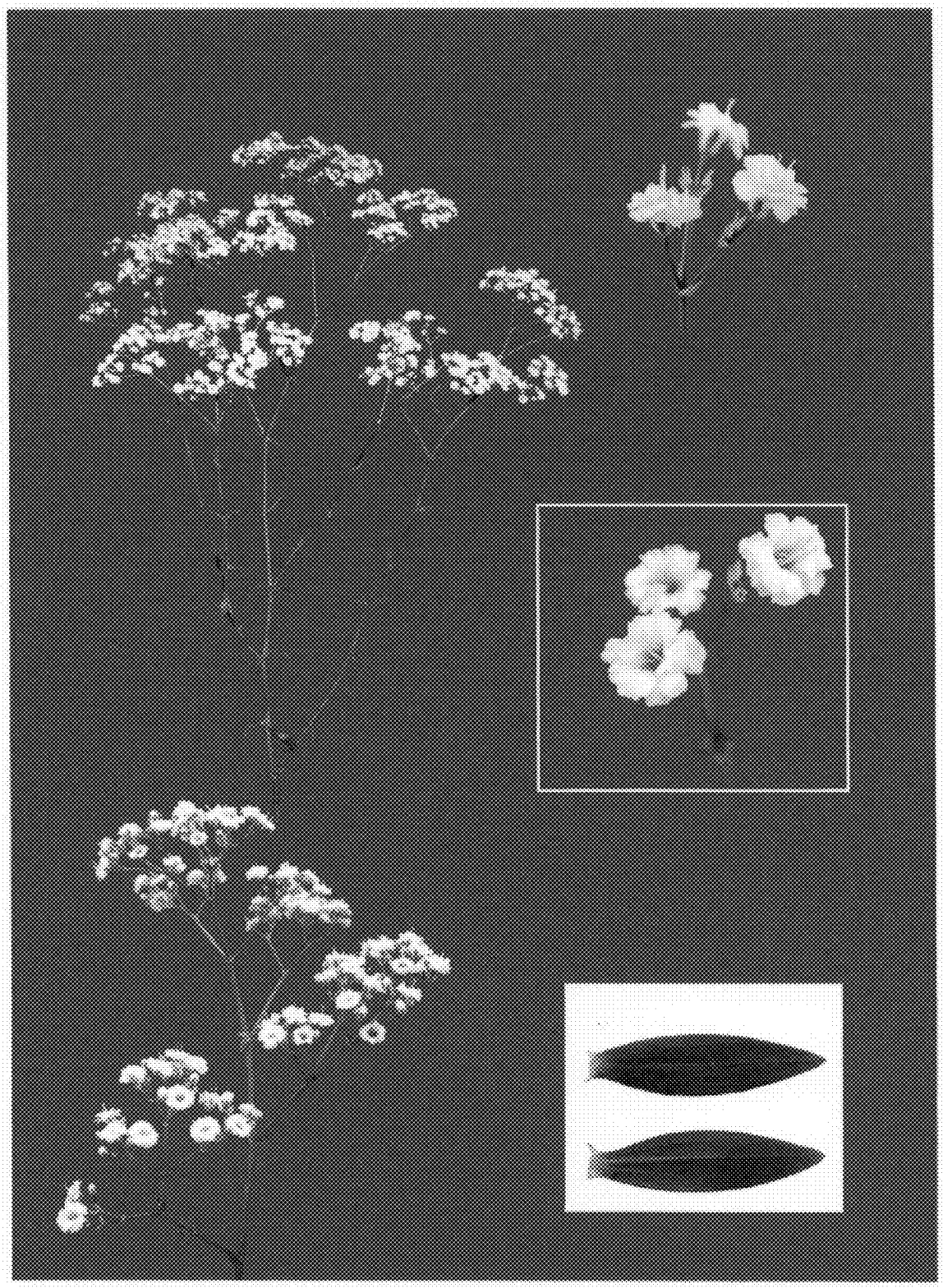

* * * * *